United States Patent [19]

Shearer et al.

[11] Patent Number: 5,874,472

[45] Date of Patent: Feb. 23, 1999

[54] AMINOACID DERIVATIVES AS NO SYNTHASE INHIBITORS

[75] Inventors: Barry George Shearer, Cary, N.C.; Karl Witold Franzmann; Harold Francis Hodson, both of Beckenham, Great Britain

[73] Assignee: Glaxo Wellcome Inc., Research Triangle Park, N.C.

[21] Appl. No.: 569,085

[22] PCT Filed: Jun. 20, 1994

[86] PCT No.: PCT/GB94/01325

§ 371 Date: Mar. 18, 1996

§ 102(e) Date: Mar. 18, 1996

[87] PCT Pub. No.: WO95/00505

PCT Pub. Date: Jan. 5, 1995

[30] Foreign Application Priority Data

Jun. 21, 1993 [GB] United Kingdom ............... 9312761

[51] Int. Cl.[6] .................... A61K 31/195; A61K 31/38; C07C 241/00; C07C 233/00

[52] U.S. Cl. ..................... 514/565; 514/538; 514/619; 514/620; 514/438; 514/447; 514/472; 514/481; 514/345; 514/352; 514/369; 514/370; 562/439; 560/34; 564/163; 564/164; 549/68; 549/76; 549/475; 549/476; 549/478; 549/479; 546/290; 546/296; 546/297; 546/304; 546/312; 548/182; 548/183; 548/184; 548/194

[58] Field of Search ................ 562/439; 560/34; 564/164, 163; 549/68, 76, 475, 6, 8, 9; 514/565, 538, 619, 620, 438, 447, 472, 481, 345, 352, 369, 370; 546/290, 6, 7, 304, 312; 548/182, 3, 4, 194

[56] References Cited

U.S. PATENT DOCUMENTS

| | | | |
|---|---|---|---|
| 4,789,681 | 12/1988 | Sportoletti et al. | 514/392 |
| 4,992,463 | 2/1991 | Tjoeng et al. | 514/438 |
| 5,028,627 | 7/1991 | Kilbourn et al. | 514/565 |
| 5,081,148 | 1/1992 | Braquet et al. | 514/162 |
| 5,281,627 | 1/1994 | Griffith | 514/565 |
| 5,318,992 | 6/1994 | Whitten et al. | 514/565 |
| 5,352,796 | 10/1994 | Hoeger et al. | 548/265.2 |
| 5,364,884 | 11/1994 | Varma et al. | 514/551 |
| 5,439,938 | 8/1995 | Synder et al. | 514/565 |
| 5,464,858 | 11/1995 | Griffith et al. | 514/399 |
| 5,478,946 | 12/1995 | Marad et al. | 548/215 |
| 5,585,402 | 12/1996 | Moncada et al. | 514/464 |

FOREIGN PATENT DOCUMENTS

| | | |
|---|---|---|
| A-0446699 | 9/1991 | European Pat. Off. . |
| A-2240041 | 7/1991 | United Kingdom . |
| WO/91/04024 | 4/1991 | WIPO . |
| PCT/GB9202387 | 7/1993 | WIPO . |
| WO/A93/13055 | 7/1993 | WIPO . |

OTHER PUBLICATIONS

Schmidt et al., *PNAS* vol. 88, pp. 365–369 (1991).
Mayer et al., *FEBS Letters.*, vol. 288, pp. 187–191 (1991).
Bredt and Snyder, *PNAS*, vol. 87, pp. 682–685 (1990).
Chemical Abstracts, vol. 89, No. 23, (Dec. 1978), Columbus, Ohio, Abstract No. 191755, C.W.I. Owens, "Induction of lysinuria in the rat by two para–substituted guanidinophenylalanines", p. 131; col. 1.
Owens, C.W.I., Clin. Sci. Mol. Med., vol. 54, pp. 673–677 (1978).
Moncada et al., *Biochemical Pharmacology*, vol. 38, pp. 1709–1715 (1989).
Moncada et al., *Pharmacological Reviews*, vol. 43, pp. 109–142 (1991).
O'Donnell et al. *Tetrahedron Letters*, No. 30, pp. 2641–2644 (1978).
Takido, Y, Itabashi, K. *Synthesis*, pp. 817–819 (1987).
Burke et al., *Synthesis*, pp. 1019–1020 (1991).
Elliott et al., Bacteriostasis in the Amino–Acid series. part II. Further Studies with Alanine Derivatives, *J. Chem. Soc.* pp. 1374–1378 (1949).

Primary Examiner—Deborah C. Lambkin
Attorney, Agent, or Firm—Lorie Ann Morgan

[57] ABSTRACT

Compounds of formula (I) and salts, esters and amides thereof, wherein $R^1$ is a $C_{1-6}$ straight or branched chain alkyl group, a $C_{3-6}$ cycloalkyl group, a thiol group optionally substituted by a $C_{1-6}$ alkyl group, or an amino group optionally substituted by one or two alkyl or alkenyl groups; $R^2$ is H, $C_{1-7}$ straight or branched chain alkyl, $C_{3-6}$ cycloalkyl, $C_{2-7}$ alkenyl or benzyl; A is a 5 or 6 membered aromatic carbocyclic or heterocyclic ring which may optionally be substituted by one or more suitable substituents such as $C_{1-6}$ alkyl, $C_{1-6}$ alkoxy, hydroxy, halo, nitro, cyano, trifluoro $C_{1-6}$ alkyl, amino, $C_{1-6}$ alkylamino or di $C_{1-6}$ alkylamino; r is 0, 1 or 2; their use in medicine and in particular for conditions requiring inhibition of the NO Synthase enzyme, pharmaceutical formulations and processes for the preparation thereof are disclosed.

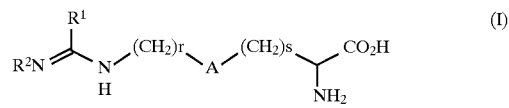

7 Claims, No Drawings

AMINOACID DERIVATIVES AS NO SYNTHASE INHIBITORS

This is a 371 of PCT/GB94/01325 Jun. 20, 1994.

The present invention relates to amino acid derivatives which contain an aromatic ring, to methods for their manufacture, to pharmaceutical compositions containing them and to their use in therapy, in particular their use as selective inhibitors of nitric oxide synthase.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amyl nitrite, glyceryltrinitrite and other nitrovasodilators. The recent identification of EDRF as NO has coincided with the discovery of a biochemical pathway by which NO is synthesised from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological reviews*, 43, 109–142 (1991)). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase isoenzymes as follows:

(i) a constitutive, $Ca^{++}$/calmodulin dependent enzyme, located in the endothelium, that releases NO in response to receptor or physical stimulation;

(ii) a constitutive, $Ca^{++}$/calmodulin dependent enzyme, located in the brain, that releases NO in response to receptor or physical stimulation;

(iii) a $Ca^{++}$ independent enzyme which is induced after activation of vascular smooth muscle, macrophages, endothelial cells, and a number of other cells by endotoxin and cytokines. Once expressed this inducible NO synthase synthesises NO for long periods.

The NO released by the constitutive isoenzyme acts as a transduction mechanism underlying several physiological responses. The NO produced by the inducible isoenzyme acts as a cytoxic molecule for tumour cells and invading microorganisms. It also appears that the adverse effects of excess NO production, in particular pathological vasodilation and tissue damage, may result largely from the effects of NO synthesised by the inducible NO synthase.

The NO synthase inhibitors proposed for therapeutic use so far, such as L-NMMA and nitroarginine, are non-selective in that they inhibit both the constitutive and the inducible NO synthase. Use of such a non-selective NO synthase inhibitor would require great care to be taken in order to avoid the potentially serious consequences of over-inhibition of the other isoenzymes. Thus, whilst non-selective NO synthase inhibitors have therapeutic utility provided that appropriate precautions are taken, NO synthase inhibitors which are selective in the sense that they inhibit one NO-synthase isoenzyme to a considerably greater extent compared to one or both of the other isoenzymes would be of even greater therapeutic benefit and much easier to use.

Patent application PCT/GB9202387 discloses a class of amidino derivatives of the formula (0)

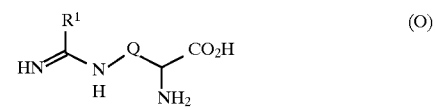

and salts and pharmaceutically acceptable esters and amides thereof, in which:

$R^1$ is a $C_{1-6}$ straight or branched chain alkyl group, a $C_{2-6}$ alkenyl group, a $C_{2-6}$ alkynyl group, a $C_{3-6}$ cycloalkyl group or a $C_{3-6}$ cycloalkyl $C_{1-6}$ alkyl group;

Q is an alkylene, alkenylene or alkynylene group having 3 to 6 carbon atoms and which may optionally be substituted by one or more $C_{1-3}$ alkyl groups, a group of formula —$(CH_2)p$—X—$(CH_2)q$— where p is 2 or 3, q is 1 or 2 and X is $S(O)_x$ where x is 0, 1 or 2, or X is O or $NR^2$ where $R^2$ is H or $C_{1-6}$ alkyl; or a group of formula —$(CH_2)_r$—A—$(CH_2)_s$— where r is 0, 1 or 2, s is 0,1 or 2 and A is a 3 to 6 membered carbocyclic or heterocyclic ring which may optionally be substituted by one or more suitable suitable substituents such as $C_{1-6}$ alkyl, $C_{1-6}$ alkoxy, hydroxy, halo, nitro, cyano, trifluori $C_{1-6}$ alkyl, amino, $C_{1-6}$ alkylamino or di $C_{1-6}$ alkylamino, which have activity as nitric oxide synthase inhibitors.

Chemical Abstracts, vol.89, abstract no. 191755v demonstrates that 4-guanidino phenylalanine and 4-guanidinomethylphenylalanine increased the renal excretion of lysine and to some extent cystine in the phenylalanine-loaded rat.

It has now been found that a particular group of compounds are inhibitors of NO synthase. Accordingly the present invention provides compounds of formula (I),

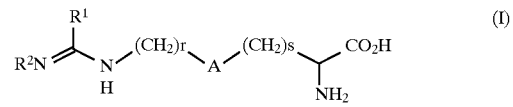

or salts, esters or amides thereof, wherein $R^1$ is a $C_{1-6}$ straight or branched chain alkyl group, a $C_{3-6}$ cycloalkyl group, a thiol group optionally substituted by a $C_{1-6}$ alkyl group, or an amino group optionally substituted by one or two alkyl or alkenyl groups; $R^2$ is H, $C_{1-7}$ straight or branched chain alkyl, $C_{3-6}$ cycloalkyl, $C_{2-7}$ alkenyl, or benzyl; A is a 5 or 6 membered aromatic carbocyclic or heterocyclic ring which may optionally be substituted by one or more suitable substituents such as $C_{1-6}$ alkyl, $C_{1-6}$ alkoxy, hydroxy, halo, nitro, cyano, trifluoro $C_{1-6}$ alkyl, amino, $C_{1-6}$ alkylamino or di $C_{1-6}$ alkylamino; r is 0, 1 or 2; s is 0, 1 or 2; with the exception of 4-guanidino-phenylalanine.

Compounds of formula (I) include those of formula (II)

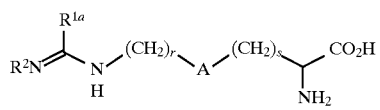

and salts, esters and amides thereof, wherein $R^{1a}$ is a $C_{1-6}$ straight or branched chain alkyl group, a $C_{3-6}$ cycloalkyl group, a $C_{1-6}$ straight or branched chain alkylthio group, or an amino group optionally substituted by one or two alkyl or alkenyl groups; $R^2$ is H, $C_{1-7}$ straight or branched chain alkyl, $C_{3-6}$ cycloalkyl, $C_{2-7}$ alkenyl, or benzyl; A is a 5 or 6 membered aromatic carbocyclic or heterocyclic ring which may optionally be substituted by one or more suitable substituents such as $C_{1-6}$ alkyl, $C_{1-6}$ alkoxy, hydroxy, halo, nitro, cyano, trifluoro $C_{1-6}$ alkyl, amino, $C_{1-6}$ alkylamino or di $C_{1-6}$ alkylamino; r is 0, 1 or 2; s is 0, 1 or 2; with the exception of 4-guanidino-phenylalanine and 4-guanidinomethyl phenylalanine.

Preferably when $R^2$ is H, $R^1$ is not a $C_{1-6}$ straight or branched chain alkyl group.

The term "heterocyclic ring" should be taken to mean a ring which contains one or more heteratoms selected from N, O and S.

When $R^1$ is SH and $R^2$ is H, the compound can exist in tautomeric form, and the present invention is intended to intended all possible tautomers.

Suitably:

$R^1$ is a $C_{1-3}$ straight or brarched chain alkyl group, a thiol group optionally substituted by a $C_{1-3}$ straight or branched chain alkyl group, or an amino group optionally substituted by $C_{1-3}$ alkyl, $C_{2-3}$ alkenyl or cyclopropyl;

$R^2$ is H, $C_{1-3}$ straight or branched chain alkyl, $C_{3-6}$ cycloalkyl, $C_{2-3}$ alkenyl or benzyl;

A is a 5- or 6- membered aromatic ring optionally containing one or two heteroatoms selected from O, S or N;

r is 0 or 1 or 2 and s is 0,1 or 2.

Suitably when $R^2$ is H, $R^1$ is not a $C_{1-3}$ straight or branched chain alkyl group.

It has also been found that compounds of formula (IA), (IB) or (IC).

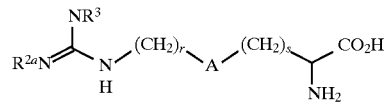

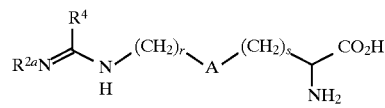

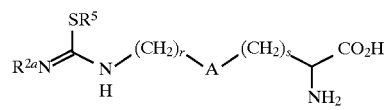

and salts, esters and amides thereof, wherein $R^{2a}$ is H, methyl, ethyl, propyl, iso-propyl, $C_{3-6}$ cycloalkyl, allyl or benzyl; $R^3$ hydrogen, $C_{1-6}$ alkyl, $C_{2-6}$ alkenyl or $C_{1-6}$ cycloalkyl; $R^4$ is a $C_{1-6}$ straight or branched chain alkyl group; $R^5$ is hydrogen or a $C_{1-6}$ straight or branched chain alkyl group; r is 0 or 1; s is 0,1 or 2; and A is selected from

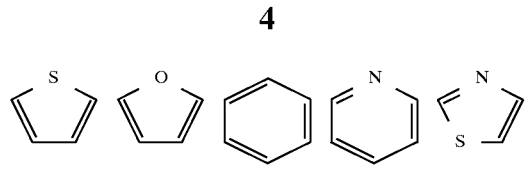

with the exception of 4-guanidino-phenylalanine, are potent inhibitors of NO synthase, and accordingly such compounds provide a further aspect of the invention.

Preferably $R^3$ is hydrogen, $C_{1-3}$ alkyl, $C_{2-3}$ alkenyl or cyclopropyl; $R^4$ is $C_{1-3}$ alkyl; and $R^5$ is hydrogen or $C_{1-3}$ alkyl.

Preferably A is

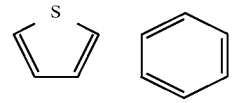

Examples of such compounds include:
3-(5-N'-methylguanidino-2-thienyl)-DL-alanine
3- (5-guanidino-2-thienyl)-DL-alanine
2- guanidino-DL-phenylalanine
3-(5-S-ethylisothioureido-2-thienyl)-DL-alanine
3-(5-N'-cyclopropylguanidino-2-thienyl)-DL-alanine
3-(5-N'-allylguanidino-2-thienyl)-DL-alanine
2-thioureido-DL-phenylalanine
2-(S-methylisothioureido)-DL-phenylalanine
2-(S-ethylisothioureido)-DL-phenylalanine
2-(N'-methylguanidino)-DL-phenylalanine
2-(N'-cyclopropylguanidino)-DL-phenylalanine
2-((1-iminoethyl)amino)-DL-phenylalanine
3-guanidino-DL-phenylalanine
3-acetamidino-DL-phenylalanine
4-Acetamidino-DL-phenylalanine
3-N-methylguanidino-DL-phenylalanine
4-N-methylguanidino-DL-phenylalanine
3-(5-(1-iminoethyl)amino)-2-thienyl)-DL-alanine
3-(5-(N'-methylguanidino)methyl)-2-thienyl)-DL-alanine
3-(5-(N'-cyclopropylguanidine)methyl)-2-thienyl)-DL-alanine
3-(5-((S-methylisothioureido)methyl)-2-thienyl)-DL-alanine
3-(5-((S-ethylisothioureido)methyl)-2-thienyl)-DL-alanine
2-(5-S-methylisothioureido-2-thienyl)-DL-glycine
2-(5-S-ethylisothioureido-2-thienyl)-DL-glycine
3-(S-methylisothioureido)-DL-phenylalanine
3-(S-ethylisothioureido)-DL-phenylalanine
4-thioureido-L-phenylalanine
4-(S-methylisothioureido)-L-phenylalanine
4-(S-ethylisothioureido)-L-phenylalanine and salts, esters and amides thereof.

The compounds of formula (I) may include a number of asymmetric centres in the molecule depending on the precise meaning of the various groups and formula (I) is intended to include all possible isomers, either individually or admixed in any proportions.

The compounds of formula (I) all include an asymmetric centre in the group

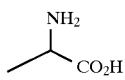

and although the natural L or (S) chirality is preferred, it is again intended that the formula should include all possible isomers.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, benzenesulphonic, and isethionic acids. Salts of the compounds of formula (I) can be made by reacting the appropriate compound in the form of the free base with the appropriate acid.

Pharmaceutically acceptable esters and amides of the compounds of formula (I) may have the —$CO_2H$ end group replaced by —$CO_2R^3$ where $R^3$ is for example $C_{1-6}$ alkyl, aryl or aryl $C_{1-3}$ alkyl or —$COR^4$ where $R^4$ is the residue of a suitable $C_{2-12}$ natural or synthetic amino acid.

A further aspect of the present invention provides a compound of formula (I) as hereinbefore defined, or 4-guanidino-DL-phenylalanine, and pharmaceutically acceptable salts, esters and amides thereof for use in medicine, and in particular for the treatment of conditions where there is an advantage in inhibiting NO production from L-arginine by the action of NO synthase.

According to a further aspect of the present invention there is provided the use of a compound of formula (I) as hereinbefore defined, or 4-guanidino-DL-phenylalanine, and pharmaceutically acceptable salts, esters and amides thereof in the manufacture of a medicament for the treatment of a condition where there is an advantage in inhibiting NO production by the action of NO synthase.

In a yet further aspect, the present invention provides a method of treatment of a human or animal body suffering from a condition where there is an advantage in inhibiting NO production from L-arginine by the action of NO synthase, comprising administering a pharmaceutically effective amount of a compound of formula (I) as hereinbefore defined or 4-guanidino-DL-phenylalanine, and pharmaceutically acceptable salts, esters and amides thereof to the human or animal body in need of such treatment.

The use of 4-guanidino-phenylalanine in accordance with the present invention is included.

Conditions in which there is an advantage in inhibiting NO production from L-arginine by the action of NO synthase include systemic hypotension associated with septic shock or induced by a wide variety of agents.

Some compounds of the present invention selectively inhibit the endothelial constitutive NO synthase enzyme and may be of use in the treatment of conditions requiring such selective inhibition; for example a selective inhibitor of the endothelial constitutive NO synthase may directly increase vascular resistance.

As used herein, reference to "treatment" of a patient is intended to include prophylaxis.

The activity of compound of the formula (I) as inhibitors of isolated NO synthase isozymes has been demonstrated against NO synthase isoenzymes isolated from the human placenta, the human brain and carcinoma cells. It is noted that the NO synthase isolated from human placenta most probably represents the endothelial constitutive isoenzyme.

Whilst it may be possible for the compounds of formula (I) to be administered as the raw chemical, it is preferable to present them as a pharmaceutical formulation. According to a further aspect, the present invention provides a pharmaceutical formulation comprising a compound of formula (I) as hereinbefore defined, or 4-guanidino-DL-phenylalanine, or a pharmaceutically acceptable salt, ester or amide thereof, together with one or more pharmaceutically acceptable carriers therefor and optionally one or more other therapeutic ingredients. The carrier(s) must be "acceptable" in the sense of being compatible with the other ingredients of the fomulation and not deleterious to the recipient thereof.

The formulations include those suitable for oral, parenteral (including subcutaneous, intradermal, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt, ester or amide thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.1 to 500 mg/kg per day. The dose range for adult humans is generally from 5 mg to 35 mg/day and preferably 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity.

The invention further includes a process for the preparation of compounds of formula (I).

Compounds of formula (I) may prepared:

(a) By deprotection of a compound of formula (III)

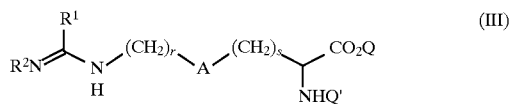

wherein $R^1$, $R^2$, A, r and s are as hereinbefore defined and Q is H or a protecting group and Q' is a protecting group. Examples of suitable protecting groups include tertbutoxycarbonyl, benzyloxycarbonyl, ethyl, tert-butyl, benzyl etc. The deprotection may be carried out by standard methods known in the art, for example by reaction with hydrochloric acid in dioxane or trifluoroacetic acid in dichloromethane, at a non-extreme temperature of from $-5°$ C. to $100°$ C., preferably room temperature, or by hydrogenolytic cleavage using hydrogen over a catalyst, for example palladium/charcoal.

Compounds of formula (III) may be made by the reaction of a compound of formula (IV)

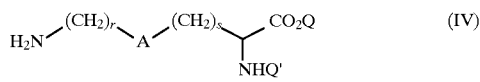

wherein A, r, s, Q and Q' are as hereinbefore defined (i) with an isothiocyanate of the formula $R^4NCS$ wherein $R^4$ is $R^2$ or benzoyl. This reaction is conveniently carried out in a polar solvent, for example a ketone such as acetone, at a non-extreme temperature such as $-20°$ C. to $50°$ C., preferably $-5°$ C. to $25°$ C. and most preferably $0°$ C., followed by alkylation with $R^3X$ wherein $R^3$ is as hereinbefore defined and X is an appropriate leaving group such as halo, mesylate or triflate. In the case where $R^4$ is benzoyl, the benzoyl may be removed by treatment with base such as sodium hydroxide prior to alkylation. The $R^1$ group ($SR^3$) may optionally be converted to another $R^1$ group, for example by reaction with a suitable amine such as $NH_3$;

(ii) with thiophosgene. The reaction may be carried out in a biphasic mixture of an aqueous and non-aqueous solvent such as water and dichloromethane at room temperature. Treatment with a suitable amine, for example ammonia will yield the corresponding compound of formula (III);

(iii) with an ethaniminium salt, such as 1-benzylthioethaniminium bromide. The reaction may suitably be carried out in an aqueous solvent, for example ethanol, at a non-extreme temperature of from $-25°$ C. to $100°$ C., suitably $5°$ C. to room temperature and preferably $0°$ C.

The compounds of formula (IV) may be converted conveniently to compounds of formula (I) in situ without isolation of the intermediates of formula (III)

Compounds of formula (IV) may be prepared by methods known in the art, for example by reduction of a nitro group, from a compound of formula (V),

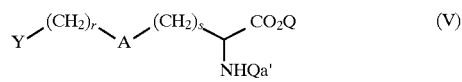

wherein Y is nitro, azido, cyano or a protected amino group ($NHQ_b'$). A and Q are as hereinbefore defined, $Q_a'$ and $Q_b'$ are different Q' groups as hereinbefore defined.

Compounds of fomula (V) may be prepared from compounds of formula (VI)

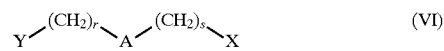

wherein Y, A and X are as hereinbefore defined by a displacement reaction by methods known in the art, such as with a glycine α-carbanion equivalent for example as O'Donnell's reagent (O'Donnell et al. Tett. Let. 1978, 30, p.2641–2644).

(b) By the hydrolysis of a compound of formula (VII)

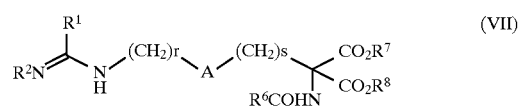

wherein $R^1$, $R^2$, A, r and s are as hereinbefore defined and $R^6$, $R^7$ and $R^8$ are independently selected from $C_{1-4}$ alkyl. The reaction may be carried out by acid hydrolysis in an acidic aqueous solution, for example 50% concentrated hydrochloric acid in water, at a non-extreme temperature of for example $0°$ C. to $150°$ C., and suitably the reflux temperature.

Compounds of formula (VII) may be prepared by the reaction of a compound of formula (VIII)

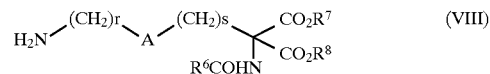

wherein $R^6$, $R^7$, $R^8$, A, r and s are as hereinbefore defined, with a compound of formula (IX)

wherein $R^1$ and $R^2$ are as hereinbefore defined and L is a leaving group. The reaction is carried out in a suitable solvent, for example a polar solvent such as water or a lower alcohol or tetrahydrofuran, at a non-extreme temperature of from 0° C. to 50° C. and preferably at room temperature. Suitable leaving groups include chloro, —$SR^9$, —$OR^9$ and —$SO_3R^9$ wherein $R^9$ is a $C_{1-6}$ alkyl group, preferably methyl or ethyl, or phenyl $C_{1-6}$ alkyl, preferably benzyl.

Compounds of formula (VIII) may be prepared as hereinbefore described for compounds of formula (IV). Compounds of formula (IX) are commercially available or may be prepared by methods readily known to one skilled in the art.

The present invention will now be described by way of example only:

EXAMPLE 1

Preparation of 3-(5-N'-methylguanidino-2-thienyl)-DL-alanine

A. Preparation of 2-hydroxymethyl-5-nitro-thiophene

Sodium borohydride (5.50 g, 145.4 mmol;) was added to a stirred, cooled solution of 5-nitro-2-thiophenecarboxaldehyde (22.0 g, 140.0 mmol) in tetrahydrofuran (500 ml). The resulting mixture was quenched with saturated aqueous ammonium chloride and warmed to room temperature. Tetrahydrofuran was removed at reduced pressure and the remaining aqueous layer was extracted with ethyl acetate. The organic layer was washed with brine and dried over magnesium sulphate. The solvent was removed at reduced pressure to give 2-hydroxymethyl-5-nitro-thiophene (18.8 g, 84%) as a brown oil which was used without further purification.

B. Preparation of 2-bromomethyl-5-nitrothiophene

To a stirred solution of 2-hydroxymethyl-5-nitro-thiophene (18.8 g, 118 mmol) in dichloromethane (500 ml) at 0° C. was added triphenylphosphine (3 1.5 g, 120 mmol) followed by carbon tetrabromide (39 g, 118 mmol). The mixture was stirred for 2 hours, poured into half saturated brine and extracted with dichloromethane. The organic layer was dried over magnesium sulphate and the solvent removed at reduced pressure. The crude product was purified by silica gel chromatography using 15% ethyl acetate/hexane as the eluant to give 2-bromomethyl-5-nitrothiophene (19 g, 61%) as a brown oil.

C. Preparation of Ethyl-N-diphenylmethylene-3-(5-nitro-2-thienyl)-DL-alaninate.

To a stirred solution of diisopropylamine (8.81 g, 87.0 mmol) in tetrahydrofuran (300 ml) at 0° C. was added 1.6M n-butyllithium in hexanes (54 ml, 86.4 mmol) over a 10 minute period. The resulting yellow mixture was stirred for 30 minutes, cooled to −78° C. and hexamethylphosphoramide (15.5 g, 86.2 mmol) was added. To this mixture was added ethyl N-(diphenylmethylene) glycinate (23.0 g, 86.0 mmol) in tetrahydrofuran (100 ml) over a 20 minute period. The dark orange mixture was stirred for 1 hour and then a solution of 2-bromomethyl-5-nitrothiophene (19.0 g, 85.6 mmol) in tetrahydrofuran (100 ml) was added over a 20 minute period. The mixture was stirred for 1 hour and then warmed to 0° C. After quenching with approximately 150 ml of ice-cold water, the mixture was concentrated at reduced pressure. The remaining aqueous layer was extracted twice with ethyl acetate. The combined organic layers were washed with brine and dried over magnesium sulphate. The solvent was removed at reduced pressure and the resulting dark brown oil was filtered through silica gel eluting with 25% ethyl acetate/hexane to remove excess diisopropylamine . The filtrate was concentrated at reduced pressure and the resulting dark brown oil was placed in vacuo overnight. Ethyl N-diphenylmethylene-3-(5-nitro-2-thienyl)-DL-alaninate (35.3 g) was obtained as a viscous dark brown oil. The product was used without further purification.

The following intermediates were prepared by an analagous method:

| Intermediate Name | Mpt/°C. |
|---|---|
| 3C Ethyl N-diphenylmethylene-2-nitro-DL-phenylalaninate (prepared from 2-nitrobenzyl bromide available from Aldrich) | 70–71 |
| 4C Tert-butyl N-diphenylmethylene-3-(5-nitro-2-thienyl)-DL-alaninate (prepared from intermediate 1B) | Oil |

D. Preparation of Ethyl 3-(5-nitro-2-thienyl)-DL-alaninate

To a stirred solution of crude ethyl N-diphenylmethylene-3-(5-nitro-2-thienyl)-DL-alaninate (35.3 g, 85.6 mmol) in diethylether (350 ml) was added 1N aqueous hydrochloric acid (350 ml, 350 mmol). The biphasic mixture was allowed to stir overnight. The two layers were separated and the ether layer was discarded. The aqueous layer was placed in an ice bath and the pH was adjusted to approximately 8 by the addition of 2N aqueous sodium hydroxide. The aqueous layer was extracted twice with dichloromethane and the combined organic layers washed with brine and dried over magnesium sulphate. The solvent was removed at reduced pressure to give a dark brown oil which was placed in vacuo. Ethyl 3-(5-nitro-2-thienyl) DL-alaninate (16.0 g) was obtained as a dark brown oil that was used without further purification.

The following intermediates were prepared by an analagous method:

| Intermediate Name | Mpt/°C. |
|---|---|
| 3D | Ethyl 2-nitro-DL-phenylalaninate | Oil |
| 4D | Tert-butyl 3-(5-nitro-2-thienyl)-DL-alaninate | Oil |

E. Preparation of Ethyl-N-(tert-butoxycarbonyl)-3-(5-nitro-2-thienyl) DL-alaninate)

To a stirred solution of ethyl 3-(5-nitro-2-thienyl)-DL alaninate (16.0 g 65.5 mmol) in dichloromethane (200 ml) at 0° C. was added triethylamine (7.26 g, 71.7 mmol) followed by di-tert-butyl dicarbonate (16.3 g,74.7 mmol) The mixture was allowed to warm to room termperature and stirred overnight. The mixture was poured into water and extracted twice with dichloromethane. The combined organic layers were washed with brine and dried over magnesium sulphate. The solvent was removed at reduced pressure. The crude product was chromatographed on silica gel eluting with 1:3 ethyl acetate: hexane to give a dark brown oil. This oil was cystallized from ethyl acetate/hexane at −78° C. to provide 14.9 g of ethyl N-(tert-butoxycarbonyl)-3-(5-nitro-2-thienyl)-DL-alaninate as a pale yellow solid. The mother liquor was concentrated at reduced pressure and purified by silica gel chromatography eluting with 1:3 ethyl acetate-:hexane to provide an additional 2.53 g of solid for a total yield of 17.4 g (59%) of desired product. Melting point=59° C.

The following intermediates were prepared by an analagous method:

| Intermediate Name | Mpt/°C. |
|---|---|
| 3E Ethyl N-(tert-butoxycarbonyl)-2-nitro-DL-phenylalaninate | 97–99 |
| 4E Tert-butyl N-(tert-butoxycarbonyl)-3-(5-nitro-2-thienyl)-DL-alaninate 200 MHz $^1$NMR(DMSO-d$_6$) δ 1.41(18H, s), 3.07–3.41 (2H, m), 4.09(1H, m), 7.10(1H, d), 7.43(1H, d), 8.03(1H, d) | |

F. Preparation of Ethyl N-(tert-butoxycarbonyl)-3-(5-amino-2-thienyl)-DL alaninate A solution of Ethyl N-(tert-butoxycarbonyl)-3-(5-nitro-2-thienyl)-DL-alaninate (4.92 g, 14.3 mmol) in ethanol (75 ml) was hydrogenated over 10% palladium/Charcoal (2.0 g) at 25 psi for 6 hours using a Parr hydrogenation apparatus. The mixture was filtered through a pad of celite. The solvent was removed at reduced pressure to give Ethyl N-(tert-butoxycarbonyl)-3-(5-amino-2-thienyl)-DL-alaninate (4.22 g, 94%) as a dark yellow solid. Melting point=132° C.

The following intermediates were prepared by an analagous method:

| Intermediate Name | Mpt/°C. |
|---|---|
| 3F Ethyl N-(tert-butoxycarbonyl)-2-amino-DL-phenylalaninate | 93–95 |
| 4F Tert-butyl N-(tert-butoxycarbonyl)-3-(5-amino-2-thienyl)-DL-alaninate 200 MHz $^1$NMR(DMSO-d$_6$) δ 1.38(18H, s), 2.88(2H, m), 3.87(1H, m), 5.27(2H, s), 5.66(1H, d), 6.31(1H, s), 7.01(1H, d) | |

G. Preparation of Ethyl N-(tert-butoxycarbonyl)-3-(5-(3-benzoylthioureido)-2-thienyl)-DL-alaninate To a stirred solution of Ethyl N-(tert-butoxycarbonyl)-3-(5-amino-2-thienyl)-DL-alaninate (4.21 g, 13.4 mmol) in acetone (75 ml) at 0° C. was added benzoyl isothiocyanate (2.55 g 15.6 mmol). The mixture was stirred for 5 minutes at 0° C., warmed to room temperature and stirred for 2 hours. The solvent was removed at reduced pressure and the resulting oil dissolved in ethyl acetate, washed with 1N aqueous hydrochloric acid, brine and dried over magnesium sulphate. The solvent was removed at reduced pressure to give a dark green viscous oil. The crude product was purified by chromatography on silica gel eluting with 1:3 ethyl acetate/hexane to yield Ethyl N-(tert-butoxycarbonyl)-3-(5-(3-benzoylthioureido)-2-thienyl)-DL-alaninate (4.91 g, 77%) as a yellow solid.

The following intermediates were prepared by an analagous method:

| Intermediate Name | Mpt/°C. |
|---|---|
| 3G Ethyl N-(tert-butoxycarbonyl)-2-(N'-methylthioureido)-DL-phenylalanine (using methyl isothiocyanate in place of benzoyl isothiocyanate) | 84–89 |
| 4G Tert-butyl N-(tert-butoxycarbonyl)-3-(5-(3-benzoyl-thioureido)-2-thienyl)-DL-alaninate | 177 |
| 7G Ethyl 2-(3-benzoylthioureido)-N-(tert-butoxycarbonyl)-DL-phenylalaninate (prepared from intermediate 3F) | 106–108 |

H. Preparation of N-(Tert-butoxycarbonyl)-3-(5-thioureido-2-thienyl)-DL-alanine

To a stirred solution of Ethyl N-(tert-butoxycarbonyl)-3-(5-(3-benzoylthioureido)-2-thienyl)-DL-alaninate (4.90 g, 10.2 mmol) in tetrahydrofuran (100 ml) was added 2N aqueous sodium hydroxide (12 ml, 24.0 mmol). The mixture was heated to reflux for 2.5 hours and cooled to room temperature. The mixture was placed in an ice bath and carefully neutralized to approximately pH7 with concentrated hydrochloric acid. The solvent was removed at reduced pressure to a volume of approximately 20–25 ml of a dark aqueous solution, and was extracted four times with ethyl acetate. The aqueous layer was adjusted to approximately pH4 with concentrated hydrochloric acid and concentrated at reduced pressure to give a dark red gummy solid. This material was taken up into ethyl acetate. All of the combined organic layers were dried over magnesium sulphate and the solvent was removed at reduced pressure to give a dark red gummy oil. This material was purified by column chromatography on silica gel eluting with 7.5:92.5:0.5 methanol:dichloromethane: acetic acid. The fractions containing the desired product were combined and concentrated at reduced pressure. The residue was redissolved in a small amount of methanol, diluted with toluene and reconcentrated at reduced pressure to azeotropically remove any remaining acetic acid. This process was repeated three times. N-(Tert-butoxycarbonyl)-3-(5-thioureido-2-thienyl)-DL-alanine. (2.33 g, 66%) was obtained as a yellow solid.

The following intermediates were prepared by an analagous method:

| Intermediate Name | Mpt/°C. |
|---|---|
| 3H N-(tert-butoxycarbonyl)-2-(N'-methylthioureido)-DL-phenylalanine | Foam |
| 4H Tert-butyl N-(tert-butoxycarbonyl)-3-(5-thioureido-2-thienyl)-DL-alaninate 200 MHz $^1$NMR(DMSO-d$_6$) δ 1.40(18H, s), 2.90–3.15(2H, m), 3.92–4.10(1H, m), 6.51(1H, d), 6.63(1H, d), 7.14(1H, d), 7.41(1H, bs), 10.33(1H, bs) | Foam |
| 7H 2-thioureido-N-(tert-butoxy)-DL-phenylalanine | |

I. Preparation of N-(tert-butoxycarbonyl)-3-(5-S-methylisothioureido-2-thienyl-DL-alanine hydroiodide In a stirred solution of N-(tert-butoxycarbonyl)-3-(5-thioureido-2-thienyl)-DL-alanine (2.30 g, 6.66 mmol) in acetone (50 ml) was added freshly distilled nethyliodide (2.74 g, 19.3 mmol). The mixture was heated to reflux and stirred overnight. The solvent was removed at reduced pressure to give a viscous dark red oil, which was placed in vacuo and afforded a red foam. The foam was suspended in hot pentane (approximately 500 ml) and a small amount of acetone was added, forming a cloudy mixture. The mixture was diluted to approximately 700 ml with pentane, cooled to room temperature, and then placed in a freezer for 1 hour. The solid was collected and dried in vacuo. N-(tert-butoxycarbonyl)-3-(5-S-methylisothioureido-2-thienyl)-DL-alanine hydroiodide. (3.09 g,95%) was obtained.

The following intermediates were prepared by an analagous method:

| Intermediate Name | Mpt/°C. |
|---|---|
| 3I N-(tert-butoxycarbonyl)-2-(N,S-dimethylisothioureido)-DL-phenylalanine | 172–173 |
| 4I Tert-butyl N-(tert-butoxycarbonyl)-3-(5-S-ethylisothio-ureido-2-thienyl)-DL-alaninate (using iodoethane in place of methyliodide) | 94–96 |
| 8I 2-(S-methylisothioureido)-N-(tert-butoxycarbonyl)-DL-phenylalanine (prepared from intermediate 7H) | |
| 9I 2-(S-ethylisothioureido)-N-(tert-butoxycarbonyl)-DL-phenylalanine (prepared from intermediate 7H using iodoethane in place of methyl iodide) | |

J. Preparation of N-(tert-butoxcyarbonyl)-3-(5-N'-methylguanidino-2-thienyl)-DL-alanine)

A solution of methylamine (3.87 g 125 mmol) in dry ethanol (30 ml) was added to N-(tert-butoxycarbonyl)-3-(5-S-methylisothioureido-2-thienyl)-DL-alanine hydroiodide (1.00 g, 2.05 mmol) in a bomb. The bomb was sealed and placed in an oil bath heated to 80° C. and left overnight. The reaction vessel was cooled to room temperature, opened and concentrated at reduced pressure to provide a viscous dark red oil. The oil was purified by chromatography on silica gel eluting with 1:1 methanol/dichloromethane to yield N-(tert-butoxycarbonyl)-3-(5-N-methyl guanidino-2-thienyl)-DL-alanine (340 mg, 35%) as a dark orange solid.

The following intermediates were prepared by an analagous method:

| Intermediate Name | | Mpt/°C. |
|---|---|---|
| 2J | N-(tert-butoxycarbonyl)-3-(5-guanidino-2-thienyl)-DL-alanine (prepared from intermediate 1I) | Oil |
| 3J | N-(tert-butoxycarbonyl)-2-(N'-methylguanidino)-DL-phenylalanine | 190–200 |
| 5J | Tert-butyl N-(tert-butoxycarbonyl)-3-(5-N'-cyclopropyl guanidino-2-thienyl)-DL-alaninate (prepared from intermediate 4I) 200 MHz $^1$NMR(DMSO-d$_6$) δ 0.48(2H, m), 0.66(2H, m), 1.41(18H, s), 3.08(2H, m), 3.98(1H, m), 6.17(1H, s), 6.58(1H, s), 7.10(1H, d) | |
| 6J | Tert-butyl N-(tert-butoxycarbonyl)-3-(5-N'-allyl-guanidino-2-thienyl)-DL-alaninate (prepared from intermediate 4I) | wax |
| 10J | 2-(N'-methylguanidino)-N-(tert-butoxycarbonyl)-DL-phenylalanine (prepared from intermediate 8I) | |
| 11J | 2-(N'-cyclopropylguanidino)-N-(tert-butoxycarbonyl)-DL-phenylalanine (prepared from intermediate 9I) | |

K. Preparation of 3-(5-N'-methylguanidino-2-thienyl)-DL-alanine 4N hydrochloric acid in dioxane (10 ml, 40.0 mmol) was added to a stirred suspension of N-(tert-butoxycarbonyl)-3-(5-N'-methylguanidino-2-thienyl)-DL-alanine (340 mg, 0.72 mmol) in dioxane (25 ml). The mixture was stirred overnight, after which time a brown precipitate had formed. The mixture was diluted with diethylether, stirred for 10 minutes and filtered. The brown, hygroscopic solid was dried in vacuo. The crude material was purified by chromatography on silica gel eluting with methanol followed by 95:5 methanol: ammonium hydroxide. The title product (130 mg) was obtained as a brown solid which was 90–95% pure. The material was rechromatographed on silica gel eluting with methanol followed by 98:2 methanol:hydroxylamine. Mass Spec: (M+1)=243.

The following final products were made by an analagous process:

| Example No. | Compound Name | Mpt/°C. |
|---|---|---|
| 2 | 3-(5-Guanidino-2-thienyl)-DL-alanine | 158° C. dec |
| 3 | 2-Guanidino-DL-phenylalanine Mass Spec.: (M + 1)223 | |
| 4 | 3-(5-S-ethylisothioureido-2-thienyl)-DL-alanine (prepared directly from 4I) 200 MHz $^1$NMR(D$_2$O) δ 1.37(3H, t), 3.20(2H, q), 3.48(2H, d), 4.28(1H, t), 6.97(2H, dd) | |
| 5 | 3-(5-N'-cyclopropylguanidino-2-thienyl)-DL-alanine 200 MHz $^1$NMR(D$_2$O) δ 0.68(2H, m), 0.83(2H, m), 2.54(1H, m), 3.41(2H, d), 4.14(1H, t), 6.87(2H, s) | |
| 6 | 3-(5-N'-allylguanidino-2-thienyl)-DL-alanine 200 MHz $^1$NMR(D$_2$O) δ 3.43(2H, d), 3.82(2H, m), 4.17(1H, t), 5.25(2H, m), 5.84(1H, m), 6.89(2H, m) | |
| 7 | 2-thioureido-DL-phenylalanine (prepared directly from 7H) 200 MHz $^1$NMR(D$_2$O) δ 3.21(2H, m), 4.15(1H, t), 7.29(1H, m), 7.42(3H, m) | |
| 8 | 2-(S-methylisothioureido)-DL-phenylalanine (prepared directly from 8I) 300 MHz $^1$NMR(D$_2$O) δ 2.56(3H, t), 3.04(2H, m), 3.81(1H, t), 7.24(1H, m), 7.36(3H, m) | |
| 9 | 2-(S-ethylisothioureido)-DL-phenylalanine (prepared directly from 9I) 300 MHz $^1$NMR(D$_2$O) δ 1.28(3H, t), 3.00(2H, q), 3.12(2H, m), 3.87(1H, t), 7.26(1H, m), 7.37(3H, m) | |
| 10 | 2-(N'-methylguanidino)-DL-phenylalanine 200 MHz $^1$NMR(D$_2$O) δ 2.86(3H, s), 3.18(2H, m), 3.99(1H, m), 7.33(1H, m), 7.42(3H, s) | |
| 11 | 2-(N'-cyclopropylguanidino)-DL-phenylalanine 300 MHz $^1$NMR(D$_2$O) δ 0.59(2H, m), 0.73(2H, m), 2.47(1H, m), 3.03(2H, m), 3.77(1H, t), 7.20(1H, m), 7.27(3H, m) | |

EXAMPLE 12

Preparation of 3-guanidino-DL-phenylalanine

A. Preparation of 3-nitrobenzyldiethylacetamidomalonate

Diethyl acetamidomalonate (20.12 g, 92.64 mmols) was added to a solution of potassium-t-butoxide (11.48 g, 102.4 mmols) in ethanol (200 mls). 3-nitro-benzyl-bromide (20 g, 92.64 mmols) was slowly added portionwise and the reaction mixture heated to reflux for 8 hours. After cooling to room temperature, the reaction mixture was treated with distilled water (400 mls) and stirred well. The resulting creamy yellow solid was removed by filtration, washed with water, dried in a vacuum oven at approximately 60° C. to dry. 3-nitrobenzyl-diethylacetamidomalonate (26.03 g, 80%) was obtained and used without further purification. Mpt.=153°–154° C.

The following intermediate was made by an analagous method:

| Intermediate Name | |
|---|---|
| 13A | 4-nitrobenzyldiethylacetamidomalonate |

B. Preparation of 3-amino-benzyldiethylacetamido malonate (3-(2-diethylacetamido malonate) ethylaniline)

A solution of 3-nitro-benzyldiethylacetamido malonate (9 g, 25.6 mmol) in methanol (450 mls) was hydrogenated over 10% palladium/charcoal (900 mg) until the theoretical quantitity of hydrogen has been adsorbed. The reaction mixture was filtered through Hyflo and evporated to dryness to give 3-amino-benzyldiethylacetamidomalonate (7.69 g, 93%) as a pale grey solid, which was used without further purification. Mpt.=159°–160° C.

The following intermediate was prepared by an analagous method:

| Intermediate Name | | Mpt/°C. |
|---|---|---|
| 13B | 4-amino-benzyldiethylacetamidomalonate(3-(2-diethyl-acetamido malonate)ethylaniline) | 124–125 |

C. Preparation of 3-guanidino-benzyldiethylacetamido malonate

Aminoiminomethanesulphonic acid (0.423 g, 3.41 mmol) was added to a suspension of 3-aminobenzyldiethylacetamidomalonate (1 g, 3.10 mmol) in methanol (8 mls). The reaction mixture was stirred at room temperature for 5 hours and at 45° C. for 23 hours. Further aminoiminomethanesulphonic acid (38 mg, 0.1 mmol) was added and stirring continued at room temperature for 68 hours. The solvent was removed under reduced pressure, water (10 mls) was added, and 3N NaOH (ca 2.5 mls) added until the pH was greater than 7. The aqueous solution was extracted with ice cold ethyl acetate (3×30 mls), the organic layers combined and dried over sodium sulphate. Filtration, followed by evaporation of the solvent gave a pale cream glass which was purified by column chromatography eluting with 20% methanol/ethyl acetate, increasing to 10%. 880 ammonia, 30% methanol/ethyl acetate. 3-guanidino-benzyldiethylacetamido malonate (920 mg, 81%) was obtained as a hygroscopic solid.

The following intermediate was prepared by an analagous method:

| Intermediate Name | |
|---|---|
| 13C | 4-guanidino-benzyldiethylacetamido malonate |

D. Preparation of 3-guanidino-DL-phenylalanine

A 50% solution of concentrated hydrochloric acid in water (40 mls) was added to 3-guanidino-benzyldiethylacetamidomalonate (910 mg, 2.5 mmol). The reaction mixture was stirred at reflux for 15 hours. The solvent was evaporated to a third of the volume and the crude product purified by ion exchange chromatography (Dowex AG 50W-X8, 100–200 mesh resin, 16 ml wet bed volume), eluting with 0.1M ammonia solution to give a tan glass/oil. Futher purified by flash column chromatography (10% 880 ammonia/methanol) gave 3-guanidino-DL-phenylalanine (240 mg, 43%) as a tan glass.

The following compound was prepared by an analagous method:

| Example No. | Compound Name | Mpt/°C. |
|---|---|---|
| 13 | 4-Guanidino-DL-phenylalanine | 179 (eff) |

EXAMPLE 14

Preparation of 3-acetamidino-DL-phenylalanine

A. Preparation of 3-amino-benzyldiethylacetamido malonate 3-amino-benzyldiethylacetamido malonate was prepared according to the method described in Example 12A–B The following intermediate was prepared by an analagous method:

| Intermediate Name | | Mpt/°C. |
|---|---|---|
| 15A | 4-amino-benzyldiethyl acetamido malonate | 124–125 |

B. Preparation of 3-acetamidino-benzyldiethylacetamido malonate Sodium carbonate (2.3 g) in water (10 mls) was added to a suspension of ethylacetimidate hydrochloride (2.84 g) in ether (25 mls) and the resulting solution was shaken vigorously. The organic layer was dried over sodium sulphate; the aqueous layer further extracted with ether (25 mls) and the organic layer dried over sodium sulphate. The ether extracts were combined and filtered to give ethyl acetimidate (1.21 g, 13.97 mmol). A solution of the ethyl acetimidate in dry ether (50 mls) was treated with a solution of 3-amino-benzyldiethylacetamidomalonate (3 g, 9.32 mmol) in dry tetrahydrofuran (100 mls) and the resulting solution stirred at room temperature for 46 days. The solvent was evaporated to give a pale grey solid which was purified by flash column chromatography eluting with 40% methanol/ethyl acetate 1% 880 ammonia to give 3-acetamidino-benzyldiethylacetamido malonate (440 mg, 13%) as a pale tan glass/gum.

The following intermediate was made by an analagous method:

| Intermediate Name | | Mpt/°C. |
|---|---|---|
| 15B | 4-acetamido-benzyldiethylacetamido malonate | gum |

C. Preparation of 3-acetamidino-DL-phenylalanine 3-acetamidino-DL-phenylalanine was prepared from 3-acetamidino-benzyldiethylacetamidomalonate (310 mg 0.85 mmol) according to the method described in Example 12D. The crude product was purified by ion exchange chromatography (Dowex AG 50W X 8, 10 cm wet bed volume, 100–200 mesh) followed by flash column chromatography (1% ammonia/methanol) to yield the title product (170 mg, 90%).

The following compound was made by an analagous method:

| Example No. | Compound Name | Mpt/°C. |
|---|---|---|
| 15 | 4-Acetamido-DL-phenylalanine | 287 |

EXAMPLE 16

Preparation of 3-N-methylguanidino-DL-phenylalanine

A. Preparation of 3-amino-benzyldiethyl acetamido malonate 3-amino-benzyldiethyl acetamido malonate was prepared according to the method described in Example 12A–B.

The following intermediate was made by an analagous method:

| Intermediate Name | | Mpt/°C. |
|---|---|---|
| 17A | 4-amino-benzyldiethyl acetamido malonate | 124–125 |

B. Preparation of 3-(N-cyano) amino-benzyldiethyl acetamido malonate.

A solution of cyanogen bromide (722.4 mg, 6.82 mmol) in methanol (3 mls) was added dropwise with stirring to an ice-cooled rmixture of 3-amino-benzyldiethylacetamidomalonate (2 g, 6.21 mmol) and sodium acetate (1.425 g, 17.38 mmol) in methanol (20 mls) at 5° C. The reaction mixture was stirred at this temperature for 2.5 hours. followed by further stirring for 2.5 days at room temperature. The solvent was evaporated and the residue treated with water (10 mls), extracted with ethyl acetate (3×30 mls) and washed with 2N hydrochloric acid (3×20 mls). The organic layers were combined and dried over sodium sulphate. Filtration, followed by evaporation of the solvent gave a pale cream solid which was purified by flash column chromatography (1% methanol/ethyl acetate) to give 3-(N-cyano)amino-benzyldiethylacetamidomalonate (1.91 g, 88%) as a pale cream solid. Mpt.=139°–142° C.

The following intermediate was prepared by an analagous method:

| Intermediate Name | Mpt/°C. |
|---|---|
| 17B 4-(N-cyano) amino-benzyldiethyl acetamido malonate. | 189–192 |

C Preparation of 3-N-methylguanidino-benzyldiethyl acetamido malonate

Methylamine (33% w/w in methylated spirit, 30 mls) was added to a solution of 3-(N-cyano)amino-benzyldiethylacetamidomalonate (900 mg, 2.59 mmol) in methanol (50 mls) in a 113 ml bomb. The bomb was heated at 70° C. for 17 hours. The solvent was remove to give 3-N-methylguanidino-benzyl diethylacetamidomalonate (1.34 g, >100%) as a tan oil which was used without further purification.

The following intermediate was prepared by an analagous method:

| Intermediate Name | Mpt/°C. |
|---|---|
| 17C 4-N-methylguanidino-benzyldiethyl acetamido malonate | glass |

D Preparation of 3-N-methylguanidino-phenylalanine

3-N-methylguanidino-phenylalanine was prepared according to the method described in example 12D. The crude product was purified by HPLC to yield the title compound (202 mg, 24%) as a cream glass.

The following compound was prepared by an analagous method:

| Example No. | Compound Name | Mpt/°C. |
|---|---|---|
| 17 | 4-N-methylguanidino-DL-phenylalanine | glass |

EXAMPLE 18

Preparation of 3-(5-(1-iminoethyl)amino)-2-thienyl)-DL-alanine

A. Preparation of tert-butyl N-(tert-butoxycarbonyl)-3-(5-(1-iminoethyl)amino)-2-thienyl)-DL-alaniate To a stirred, cooled (0° C.) solution of tert-butyl N-(tert-butoxycarbonyl)-3-(5-amino-2-thienyl)-DL-alaninate (590 mg, 1.72 mmol), prepared as described in Example 1A–1F, in EtOH (15 mL) was added 1-benxylthioethaniminium bromide (420 mg, 1.71 mmol), prepared according to the procedure of Takido, Y.; Itabashi, K. *Synthesis* 1987, 817–819. After stirring for 10 minutes, the mixture was concentrated at reduced pressure, diluted with water and washed with Et$_2$O. The aqueous layer was poured into saturated aqueous NaHCO$_3$ and extracted with Et$_2$O. The organic layer was dried over MgSO$_4$ concentrated to a volume of 30 mL and treated with 1N ethereal HCl (1.8 mL, 1.80 mmol). The resulting white suspension was stirred for 10 minutes and eventually became a viscous oil. Solvent was removed at reduced pressure. The resulting foam was dissolved in water and lyophilized overnight to afford 539 mg (75%) of the title compound as its hydrochloride salt as a white powder. 200 MHz $^1$NMR (D$_2$O) δ 1.35 (9H, s), 1.41 (9H, s), 2.34 (3H, s), 3.21 (2H, m), 4.27 (1H, m), 6.84 (1H, d), 6.91 (1H, d).

The following intermediate was prepared by an analagous method:

| Intermediate Name |
|---|
| 19A 2-((1-iminoethyl)amino)-N-(tert-butoxycarbonyl)-DL-phenylalanine |

B. Preparation of 3-(5-(1-iminoethyl)amino)-2-thienyl)-DL-alanine 3-(5-(1-iminoethyl)amino)-2-thienyl)-DL-alanine was prepared according to the method described in Example 1K to give 336 mg (68%) of a hygroscopic white powder. 200 MHz $^1$NMR (D$_2$O) δ 2.35 (3H, s), 3.43 (2H, d), 4.13 (1H, t), 6.93 (2H, m).

The following compound was made by an analagous method

| Example No. | Compound Name |
|---|---|
| 19 | 2-((1-iminoethyl)amino)-DL-phenylalanine 200 MHz $^1$NMR(D$_2$O) δ 2.42(3H, s), 3.15(2H, m), 3.97(3H, t), 7.34(1H, m) 7.47(3H, m) |

EXAMPLE 20

Preparation of 3-(5-(N'-methylguanidino)methyl)-2-thienyl)-DL-alanine

A. Preparation of N-(2-thienylmethyl)phthalimide

To a stirred mixture of 2-thienylmethylamine (49.6 g, 439 mmol) and phthalic anhydride (65.0 g, 439 mmol) in toluene (1000 mL) was added triethylamine (10.9 g, 108 mmol). The mixture was heated to reflux and water was removed via a Dean Stark trap. After 3 h, the mixture was cooled to room temperature and solvent was removed at reduced pressure. The resulting solid was recyrstallized from EtOAc to afford 83.2 g (78%) of a white solid. The $^1$H NMR spectrum was consistent for the title compound. Mpt.=124°–125° C.

B. Preparation of N-((5-formyl-2-thienyl)methyl) phthalimide

To a stirred, cooled (0° C.) solution of α,α-dichloromethyl methyl ether (30.5 g, 265 mmol) in CH$_2$Cl$_2$ (1600 mL) was added SnCl$_4$ (64.5 g, 248 mmol) over a 10 minute period. The mixture was stirred with an overhead stirrer for 20 minutes and N-(2-thienylmethyl)phthalimide (50.0 g, 205 mmol) was added. The dark purple mixture was stirred for 2 h, poured into ice cold water (1500 mL) with rapid stirring and allowed to warm to room temperature. The layers were separated and the aqueous layer was extracted with CH$_2$Cl$_2$. The combined organic layers were washed with brine and dried over MgSO$_4$. Solvent was removed at reduced pressure. The purple oil was dissolved in toluene and chromatographed on silica gel eluting with 3:7 EtOAc-hexane followed by 1:1 EtOAc-hexane to afford 23.3 g (42%) of a white solid. The $^1$H NMR spectrum was consistent for the title compound.

C. Preparation of N-((5-(hydroxymethyl)-2-thienyl)methyl) phthalimide

To a stirred, cooled (0° C.) solution of N-((5-(formyl-2-thienyl)methyl)phthalimide (28.6 g, 105 mmol) in THF (500 mL) was added NaBH$_4$ (4.32 g, 114 mmol). The mixture was stirred for 2.5 h, quenched with saturated aqueous NH$_4$Cl and warmed to room temperature. The organic solvent was removed at reduced pressure and the remaining aqueous layer was extracted twice with EtOAc. The combined organic layers were washed with brine and dried over MgSO$_4$. Solvent was removed at reduced pressure giving a yellow solid. This solid was dissolved in a minimal amount of warm EtOAc and chromatographed on silica gel eluting with 1:3 EtOAc-hexane followed by 1:1 EtOAc-hexane to afford 20.1 g (70%) of a white solid. The $^1$H NMR spectrum was consistent for the title compound. Mpt.=153° C.

D. Preparation of N-((5-(bromomethyl)-2-thienyl)methyl) phthalimide

To a stirred, cooled (0° C.) suspension of N-((5-(hydroxymethyl)-2-thienyl)-methyl)phthalimide (19.6 g, 71.7 mmol) in $CH_2Cl_2$ (500 mL) was added carbon tetrabromide (23.8 g, 71.8 mmol) followed by triphenylphosphine (18.9 g, 72.1 mmol). The mixture became homogeneous and was allowed to warm to room temperature while stirring overnight. After concentrating at reduced pressure to a volume of 50 mL at reduced pressure, the mixture was chromatographed on silica gel eluting with 1:4 EtOAc-hexane followed by 2:3 EtOAc-hexane to afford 15.6 g (65%) of a white solid. The $^1$H NMR spectrum was consistent for the title compound.

E. Preparation of ethyl N-(tert-butoxycarbonyl)-3-(5-(phthalimidomethyl)-2-thienyl)-DL-alaninate The title compound was prepared from N-((5-(bromomethyl)-2-thienyl)methyl)-phthalimide and ethyl N-(diphenylmethylene)gycinate according to the procedure described in Example 1C–1E to give 16.1 g (100%) of a viscous pale yellow oil. The $^1$H NMR spectrum was consistent for the title compound.

F. Preparation of ethyl N-(tert-butoxycarbonyl)-3-(5-aminomethyl-2-thienyl)-DL-alaninate To a stirred solution of ethyl N-(tert-butoxycarbonyl)-3-(5-(phthalimidomethyl)-2-thienyl)-DL-alaninate (15.4 g, 33.7 mmol) in EtOH (250 mL) was added hydrazine monohydrate (2.58 g, 51.5 mmol). The mixture was stirred overnight. The resulting thick white suspension was diluted with EtOH (100 mL) and stirring was continued overnight. The mixture was cooled to 0° C. and acidified with 1N aqueous HCl. Solvent was removed at reduced pressure to give a white solid. This solid was suspended in water and removed by filtration. The filtrate was cooled in an ice bath, adjusted to pH=10 with 1N aqueous NaOH and extracted three times with EtOAc. The combined organic layers were dried over $MgSO_4$. Solvent was removed at reduced pressure and the crude product was chromatographed on silica gel eluting with EtOAc followed by 3:97 EtOH-EtOAc to afford 6.61 g (60%) of a viscous yellow oil. The $^1$H NMR spectrum was consistent for the title compound.

G. Preparation of 3-(5-(N'-methylguanidino)methyl)2-thienyl)-DL-alanine

The title compound was prepared from ethyl N-(tert-butoxycarbonyl)-3-(5-amininomethyl-2-thienyl)-DL-alaninate according to the methods described in Example 1G–1K to afford 104 mg (16%) of a white hygroscopic powder. 200 MHz $^1$H NMR ($D_2O$) δ 2.79 (3H, s), 3.44 (2H, d), 4.21 (1H, t), 4.52 (2H, s), 6.89 (2H, d).

EXAMPLE 21

Preparation of 3-(5-(N'-cyclopropylguanidino) methyl)-2-thienyl)-DL-alanine

A. Preparation of tert-butyl N-(tert-butoxycarbonyl)-3-(5-aminomethyl-2-thienyl)-DL-alaninate The title compound was prepared from N-((5-(bromomethyl)-2-thienyl)-methyl)phthalimide and tert-butyl N-(diphenylmethylene)glycinate according to the procedure described in Example 20A–F to give 8.24 g (68%) of a viscous yellow oil. The $^1$H NMR spectrum was consistent for the title compound.

B. Preparation of tert-butyl N-(tert-butoxycarbonyl)-3-((5-thioureido)methyl-2-thienyl)-DL-alaninate To a stirred mixture of $CaCO_3$ (1.10 g, 10.9 mmol) and thiophosgene (633 mg, 5.51 mmol) in water (20 mL) was added a solution of tert-butyl N-(tert-butoxy-carbonyl)-3-(5-(aminomethyl)-2-thienyl)-DL-alaninate (1.42 g, 3.98 mmol) in $CHCl_3$ (20 mL). The biphasic mixture was stirred vigorously for 2 h and filtered. The two layers were separated and the aqueous layers was extracted with $CHCl_3$. The combined organic layers were washed with brine, dried over $MgSO_4$ and concentrated at reduced pressure. The resulting oil was dissolved in MeOH (40 mL), cooled to 0° C. and a stream of ammonia was bubbled into the solution for 10 minutes. After stirring for 3 h, the mixture was concentrated at reduced pressure and chromatographed on silica gel eluting with 3:1 EtOAc-hexane to afford 1.37 g (83%) of a foam. The $^1$H NMR spectrum was consistent for the title compound.

C. Preparation of 3-(5-(N'-cyclopropylguanidino)methyl)-2-thienyl)-DL-alanine

The title compound was prepared from tert-butyl N-(tert-butoxycarbonyl)-3-((5-thioureido)methyl-2-thienyl)-DL-alaninate and iodoethane as described in Example 1I–K to afford 114 mg (30%) of a hygroscopic white powder. 200 MHz $^1$H NMR ($D_2O$) δ 0.59 (2H, m), 0.79 (2H, m), 2.48 (1H, m), 3.41 (2H, d), 4.10 (1H, t), 4.52 (2H, s), 6.85 (1H, d), 7.90 (1H, d).

The following compounds were prepared by analagous methods

| Example No. | Compound Name |
| --- | --- |
| 22 | 3-(5-((S-methylisothioureido)methyl)-2-thienyl-DL-alanine (prepared from intermediate 21B as described in Example 1I and 1K) 200 MHz $^1$NMR($D_2O$) δ 2.57(3H, s), 3.45(2H, d), 4.21(1H, t), 4.70(2H, s), 6.89(1H, d), 6.98(1H, d) |
| 23 | 3-(5-((S-ethylisothioureido)methyl)-2-thienyl)-DL-alanine (prepared from intermediate 21B and iodoethane as described in Example 1I and 1K) 200 MHz $^1$NMR($D_2O$) δ 1.32(3H, t), 3.11(2H, q), 3.46(2H, d), 4.20(1H, t), 6.90(1H, d), 6.99(1H, d) |

EXAMPLE 24

Preparation of 2-(5-S-methylisothioureido-2-thienyl) -DL-glycine

A. Preparation of DL-methyl 2-amino-2-(2-thienyl)acetate

To dry MeOH (1000 mL) stirring at room temperature was added acetyl chloride (40.3 g, 513 mmol) over a 5 minute period. A mild exothermic reaction resulted. The mixture was stirred for 10 minutes and DL-α-amino-2-thiopheneacetic acid (40.5 g, 257 mmol) was added. The brown mixture was heated to reflux and stirred overnight. After cooling to room temperature, the mixture was concentrated to a volume of 400 mL and poured into $Et_2O$ (1500 mL). The precipitated white solid was collected and dried in vacuo to afford 49.2 g (92%) of the title compound as its hydrochloride salt. The $^1$H NMR spectrum was consistent for the title compound. An analytical sampie was recrystallized from EtOAc-hexane. Mpt.=182° C.

B. Preparation of DL-methyl 2-phthalimido-2-(2-thienyl)acetate

To a stirred suspension of DL-methyl 2-amino-2-(2-thienyl)acetate hydrochloride (47.5 g, 229 mmol) and phthalic anhydride (34.0 g, 230 mmol) in toluene (1000 mL) in a round bottom flask equipped with a Dean Stark trap was added triethylamine (25.4 g, 251 mmol). The mixture was heated to reflux and the homogeneous solution was stirred overnight. After cooling to room temperature, the mixture was washed with 1N aqueous HCl, brine and dried over $MgSO_4$. Solvent was removed at reduced pressure. The crude brown solid was dissolved in a minimal amount of EtOAc and chromatographed on silica gel eluting with 2:3 EtOAc-hexane. Recrystallization from EtOAc-hexane afforded 56.3 g (82%) of a white solid. The $^1$H NMR spectrum was consistent for the title compound. Mpt.=128° C.

C. Preparation of DL-methyl 2-N-(tert-butoxycarbonyl)-2-(5-bromomethyl-2-thienyl)acetate The title compound was prepared from DL-methyl 2-phthalimido-2-(2-thienyl)acetate according to the procedures described in Examples 20B, 20C, 20F, 1E and 20D to give 8.54 g (61%) of a yellow oil. The $^1$H NMR spectrum was consistent for the title compound.

D. Preparation of DL-methyl 2-N-(tert-butoxycarbonyl)-2-(5-azidomethyl-2-thienyl)acetate To a stirred solution of DL-methyl 2-N-(tert-butoxycarbonyl)-2-(5-bromomethyl-2-thienyl)acetate (8.54 g, 23.4 mmol) in 9:1 acetone-water (100 mL) was added sodium azide (4.51 g, 69.4 mmol). The mixture was stirred overnight. Solvent was removed at reduced pressure and the residue was dissolved in $CH_2Cl_2$, washed with water, brine and dried over $MgSO_4$. Removal of solvent at reduced pressure and chromatography on silica gel eluting with 1:9 EtOAc-hexane afforded 6.19 g (81%) of a yellow oil. The $^1$H NMR spectrum was consistent for the title compound.

E. Preparation of DL-methyl 2-N-(tert-butoxycarbonyl)-2-(5-aminomethyl-2-thienyl)acetate A stirred solution of DL-methyl 2-N-(tert-butoxycarbonyl)-2-(5-azidomethyl-2-thienyl)acetate (6.18 g, 18.9 mmol) in MeOH (100 mL) was hydrogenated over 10% Pd/C (420 mg) at 1 atm (balloon pressure) for 3 h. The mixture was filtered through Celite and the filtrate was concentrated at reduced pressure. The residue was chromatographed on silica gel eluting with EtOAc to afford 4.91 g (86%) of the title compound as a viscous yellow oil. The $^1$H NMR spectrum was consistent for the title compound.

F. Preparation of N-(tert-butoxycarbonyl)-2-(5-thioureidomethyl-2-thienyl)-DL-glycine The title compound was prepared from DL-methyl 2-N-(tert-butoxycarbonyl)-2-(5-aminomethyl-2-thienyl)acetate as described in Example 1G and 1H. The crude product was concentrated in vacuo onto silica gel and purified by silica gel chromatography eluting with 4:16:0.1 MeOH—$CH_2Cl_2$—AcOH. The isolated product was dissolved in water and lyophilized to give 3.70 g of a light orange solid. The $^1$H NMR spectrum was consistent for the title compound.

G. Preoaration of 2-(5-S-methylisothioureido-2-thienyl)-DL-glycine

The title compound was prepared from N-(tert-butoxycarbonyl)-2-(5-S-methylisothioureidomethyl-2-thienyl)-DL-glycine as described in Example 1I and 1K. Reverse phase HPLC purification eluting with 1% MeOH—$H_2O$ containing 0.1% TFA afforded 407 mg (67%) of a hygroscopic white powder. 200 MHz $^1$H NMR ($D_2O$) δ 2.56 (3H, s), 4.73 (2H, s), 5.15 (1H, s), 7.02 (1H, d), 7.10 (1H, d).

The following compound was prepared by an analagous method

| Example No. | Compound Name |
|---|---|
| 25 | 2-(5-S-ethylisothioureido-2-thienyl)-DL-glycine (prepared from intermediate 24F and iodoethane) 200 MHz $^1$NMR ($D_2O$) δ 1.29(3H, t), 3.09(2H, q), 4.73(2H, s), 1H, d), 7.09(1H, d) |

EXAMPLE 26

Preparation of 3-(S-methylisothioureido)-DL-phenylalanine

A. Preparation of methyl 2-azido-3-(3-nitroohenyl)acrylate

To a stirred, cooled (0° C.) solution of ethyl 2-azidoacetate. (13.1 g, 100 mmol), prepared according to the procedure of Burke, T. R., Jr.; Russ, P.; Lim, B. *Synthesis* 1991, 1019–1020, and 3-nitrobenzaldehyde (10.0 g, 66.0 mmol) in methanol (70 mL) was added sodium methoxide (4.30 g, 80.0 mmol). The mixture was allowed to warm slowly to room temperature while stirring overnight. The reaction mixture was filtered and evaporated to dryness. The residue was dissolved in diethyl ether, washed with water and dried over $Na_2SO_4$. Solvent was removed at reduced pressure to give a solid. Recrystallization from diethyl ether afforded 5.50 g (28%) of a yellow solid. The $^1$H NMR spectrum was consistent for the title compound. Mpt.=120°–121° C.

B. Preparation of methyl 3-amino-DL-phenylalaninate

The title compound was prepared from methyl 2-azido-3-(3-nitrophenyl)acrylate according to the procedure described in Example 1F to give 3.90 g (91%) of a light beige solid. The $^1$H NMR spectrum was consistent for the title compound. Mpt.=106°–108° C.

C. Preparation of methyl 3-amino-N- (tert-butoxycarbonyl) -DL-phenylalaninate

To a stirred, cooled (−78° C.) solution of methyl 3-amino-DL-phenylalaninate (3.90 g, 20.0 mmol) in $CH_2Cl_2$ (150 mL) was added a solution of di-tert-butyl dicarbonate (4.38 g, 20.0 mmol) in $CH_2Cl_2$ (10 mL) dropwise. After stirring for 2 h, the mixture was allowed to warm to room temperature, washed with water and dried over $Na_2SO_4$. Solvent was removed at reduced pressure to give a solid. Recrystalization from EtOAc-hexane afforded 4.30 g (73%) of solid product. The $^1$H NMR spectrum was consistent for the title compound. Mpt.=127°–128° C.

D. Preparation of N-(tert-butoxycarbonyl)-3-thioureido-DL-phenylalanine

The title compound was prepared from methyl 3-amino-N-(tert-butoxycarbonyl)-DL-phenylalaninate as descirbed in Example 1G and 1H. The crude product was chromatographed on silica gel eluting with 1:2 MeOH-EtOAc followed by 1:1 MeOH-EtOAc to give 1.38 g (64%) of a light beige solid. The $^1$H NMR spectrum was consistent for the title compound.

E. Preparation of 3-(S-methylthioureido)-DL-phenylalanine

The title compound was prepared from N-(tert-butoxycarbonyl)-3-thioureido-DL-phenylalanine as descirbed in Example 1I and 1K to give 136 mg (27%) of a hygroscopic white solid. 200 MHz $^1$NMR ($D_2O$) δ 2.66 (3H, s), 3.24 (2H, d), 4.09 (1H, t), 7.40 (4H, m).

The following compound was made by an analagous process

| Example No. | Compound Name |
|---|---|
| 27 | 3-(S-ethylisothioureido)-DL-phenylalanine (prepared from intermediate 26D and iodoethane) 200 MHz $^1$NMR($D_2O$) δ 1.38(3H, t), 3.20(2H, m), 4.03(1H, t), 7.40(4H, m) |

EXAMPLE 28

Preparation of 4-thioureido-L-phenylalanine

A. Preparation of tert-butyl N-(tert-butoxycarbonyl) 4-nitro-L-phenylalaninate

To a cooled (0° C.) solution of 4-nitro-L-phenylalanine (14.0 g, 60.1 mmol) in 1,4-dioxane (120 mL) in a 500 mL pressure bottle was added concentrated $H_2SO_4$ (13.4 mL, 241 mmol) followed by condensed isobutylene (110 mL). The reaction bottle was stoppered, warmed to room temperature and shaken overnight. Excess isobutylene was removed under vacuum and the remaining solution was poured into a stirred, cooled (0° C.) solution of triethylamine (56.4 g, 558 mmol) in water (130 mL). Di-tert-butyl dicarbonate (13.3 g, 60.9 mmol) was added in several portions. After stirring at 0° C. for 2 h, the mixture was warmed to room temperature and stirred overnight. Solvent was removed at reduced pressure. The resulting oil was dissolved in EtOAc, washed with water and dried over $Na_2SO_4$. Removal of solvent at reduced pressure and chromatography on silica gel eluting with 1:5 EtOAc-hexane followed by 1:1 EtOAc-hexane afforded 19.2 g (87%) of product. The $^1H$ NMR spectrum was consistent for the title compound. Mpt.=53°–54° C.

B. Preparation of tert-butyl N-(tert-butoxycarbonyl)-4-thioureido-L-phenylalaninate The title compound was prepared from tert-butyl N-(tert-butoxycarbonyl)-4-nitro-L-phenylalaninate as described in Examples 1F, 1G and 1H to give 1.40 g (31%) of a white solid. The $^1H$ NMR spectrum was consistent for the title compound.

C. Preparation of 4-thioureido-L-phenylalanine

The title compound was prepared from tert-butyl N-(tert-butoxycarbonyl) 4-nitro-L-phenylalaninate as described as described in Examples 1K to give 42 mg (10%) of a hygroscopic white powder.

The following compounds were prepared by an analagous method

| Example No. | Compound Name |
|---|---|
| 29 | 4-(S-methylisothioureido)-L-phenylalanine (prepared from intermediate 28B and iodomethane according to Example 1I and 1K) 200 MHz $^1NMR(D_2O)$ δ 2.64(3H, s), 3.25(2H, d), 4.15(1H, t), 7.32(2H, d), 7.41(2H, d) |
| 30 | 4-(S-ethylisothioureido)-L-phenylalanine (prepared from intermediate 28B and iodoethane according to Example 1I and 1K) 300 MHz $^1NMR(D_2O)$ δ 1.26(3H, t), 3.13(4H, m), 4.08(1H, t), 7.21(2H, d), 7.30(2H, d) |

EXAMPLE 31

Biological Activity

The activity of representative compounds of the present invention was determined in accordance with the assay herein described.

Purification of NOS from human placenta.

Amion and chorion were removed from fresh placenta, which was then rinsed with 0.9% NaCl. The tissue was homogenized in a Waring blender in 3 volumes of HEDS buffer (20 mM Hepes pH 7.8, 0.1 mM EDTA, 5 mM DTT, 0.2M sucrose) plus 0.1 mM PMSF.

The homogenate was filtered through cheesecloth and then centrifuged at 1000 g for 20 min. The supernatant was recentrifuged at 27500 g for 30 min. Solid ammonium sulfate was added to the supernatant to give 32% saturation. Precipitated protein was pelleted at 25,000 g and then redissolved in a minimal volume of HEDS buffer plus 0.1 mM PMSF, 10 μg/ml leupeptin and soybean trypsin inhibitor, and 1 μg/ml pepstatin. The redissolved pellet was centrigued at 15000 g for 10 min. To the supernatant was added ½₀ volume of 2',5' ADP agarose resin (Sigma), and the slurry was mixed slowly overnight. In morning, slurry was packed into a column. The resin was sequentially washed with HEDS, 0.5M NaCl in HEDS, HEDS, and then NOS was eluted with 10 mM NADPH in HEDS. The enzyme could be concentrated by ultrafiltration and quick frozen and stored at −70° C. without loss in activity for at least 6 months.

Assay for human placental NOS

NOS was assayed for the formation of citrulline following the procedure of Schmidt et al (PNAS 88 365–369, 1991) with these modifications: 20 mM Hepes, pH 7.4, 10 μg/ml calmodulin, 2.5 mM $CaCl_2$ 2.5 mM DTT, 125 μM NADPH 10 μM $H_4$ Biopterin, 0.5 mg/ml BSA, and 1 μM L-$[^{14}C]$ arginine (New England Nuclear). Linearity of NOS-catalyzed rate was confirmed prior to kinetic studies that used single time point determination of rate.

Purification of NOS cytokine-induced human colorectal adenocarcinoma DLD-1 cells.

DLD-1 (ATCC No. CCL 221) were grown at 37° C., 5% $CO_2$ in RPMI 1640 medium supplemented with L- glutamin, penicillin, streptomycin, and 10% heat-inactivated fetal bovine serum. Cells were grown to confluency and then the following cocktail of cytokines were added: 100 units/ml interferon-gamma, 200 units/ml interleukin-6, 10 ng/ml tumor necrosis factor, and 0.5 ng/ml interieukin-1β. At 10–24 hr post-induction, cells were harvested by scraping and washed with phosphate-buffered saline. Pelleted cells were stored at −70° C. Purification of the induced NOS was performed at 4° C. Crude extract was prepared by three cycles of freeze/thawing cells in TDGB (20 mM tris pH 7.5, 10% glycerol, 1 mM DTT, 2 μM tetrahydrobiopterin). Extract was applied directly onto a column of 2',5' ADP sepharse (Pharmacia). Resin was sequentially washed with TDGB, 0.5 M NaCl in TDGB, TDGB. NOS was eluted with 2 mM NADPH in TDGB. BSA was immediately added to give a final concentration of 1 mg/ml. NOS could be quick frozen and stored at −70° C. without loss in activity for at least 2 months.

Assay for inducible human NOs.

The formation of citrulline was assayed as described above except that 10 μM FAD was included and calmodulin and $CaCl_2$ were excluded from the assay mix.

Purification of NOS from human brain

Human brain NOS was prepared using variations of the procedures of Schmidt et al. (*PNAS* 88 365–369, 1991), Mayer et al. (*Fed. Eur. Biochem. Soc.* 288 187–191, 1991), and Bredt and Snyder, (PNAS 87 682–685, 1990). Briefly, frozen human brain (1050 gm) was homogenized in cold buffer A (50 mM HEPES, pH 7.5 (pH at RT) and 0.5 mM EDTA, 10 mM DTT, 3.6 L total volume) with a polytron. The mixture was centrifuged at 13,000 g for 1 hour and the supernatant was removed (about 2050 ml). To the supernatant, solid aimmonium sulfate (365 gm, about 30% of saturation) was added and stirred slowly for a total of 30 minutes. The precipitate was pelleted at 13,000 g for 30 minutes and the pellet was resuspended in ~400 mls of buffer A with 4 μM tetrahydrobiopterin, 1 μM FAD (Sigma), 1 μM FMN (Sigma). The solution was centrifuged at 41,000 g for 60 minutes. The supernatant was removed, frozen by pouring into liquid nitrogen, and stored overnight at −70° C. The mixture was thawed and passed through a 2',5' ADP-agarose column (0.4 g swelled in buffer A) at 4 ml/min. The column was washed with 100 ml buffer A, 200 ml buffer A with 500 mM NaCl, 100 ml Buffer A, then 30 ml buffer A with 5 mM NADPH. To the enzyme eluted from the column was added glycerol to 15%, $CaCl_2$ to 1 mM, tetrahydrobiopterin to 10 μM, tween to 0.1% and FAD, FMN to 1 μM each. The enzyme was then passed through a 1 ml calmodulin-agarose column which had been equilibrated in Buffer A, 15% glycerol and 1 mM $CaCl_2$. The column was washed with 15 ml Buffer A, 15% glycerol and 1 mM CaCl$_2$, 15 ml of Buffer A, 15% glycerol and 5 mM EDTA, and then enzyme activity was eluted with 3 ml of Buffer A, 15% glycerol and 5 mM EDTA, 1 M NaCl. To the enzyme was added tetrahydrobiopterin to 10 μM, FAD and FMN to 1 μM, and tween to 0.1%. This solution was concentrated by centriprep-30 to a volume of approximately 500 μl. Human NOS was prepared completely analogously except the calmodulin-agarose column was not used. Enzyme activity was determined as described by Schmidt et al. 1991, except that 10 μM tetrahydrobiopterin was included in the assay. The results are given in Table 1.

TABLE 1

NO Synthesis Inhibition Data

| Compound | Human Inducible Ki(μM) | Human Placental Ki(μM) | Human Brain Ki(μM) |
|---|---|---|---|
| 1 | >50 | ≦10 | ≦50 |
| 2 | ≦50 | ≦50 | ≦10 |
| 3 | ≦10 | ≦0.5 | ≦0.5 |
| 4 | >50 | ≦10 | ≦50 |
| 5 | >50 | ≦10 | ≦10 |
| 6 | ≦10 | ≦10 | ≦10 |
| 7 | ≦10 | ≦10 | ≦10 |
| 8 | ≦10 | ≦1 | ≦1 |
| 9 | ≦1 | ≦0.5 | ≦0.5 |
| 10 | ≦1 | ≦0.5 | ≦0.5 |
| 11 | ≦1 | ≦0.5 | ≦1 |
| 12 | >50 | ≦50 | ≦50 |
| 13 | >50 | >50 | >50 |
| 14 | >50 | >50 | >50 |
| 15 | >50 | >50 | >50 |
| 16 | >50 | ≦10 | ≦10 |
| 17 | >50 | ≦50 | ≦50 |
| 18 | ≦10 | ≦50 | ≦50 |
| 19 | ≦10 | ≦10 | ND |
| 20 | >50 | >50 | >50 |
| 21 | >50 | >50 | >50 |
| 22 | >50 | >50 | >50 |
| 23 | ≦10 | ≦10 | ≦10 |
| 24 | >50 | >50 | >50 |
| 25 | ≦10 | ≦50 | ≦10 |
| 26 | ≦50 | ≦10 | ≦10 |
| 27 | ≦10 | ≦10 | ≦1 |
| 28 | >50 | >50 | >50 |
| 29 | >50 | >50 | >50 |
| 30 | ≦10 | ≦0.5 | ≦0.5 |

ND = Not Determined

We claim:

1. A compound of formula (I):

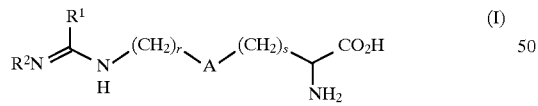

and salts, esters and amides thereof, wherein $R^1$ is a $C_{1-6}$ straight or branched chain alkyl group, a $C_{3-6}$ cycloalkyl group, a thiol group optionally substituted by a $C_{1-6}$ alkyl group, or an amino group optionally substituted by one or two alkyl or alkenyl groups;

$R^2$ is H, $C_{1-7}$ straight or branched chain alkyl, $C_{3-6}$ cycloalkyl, $C_{2-7}$ alkenyl, or benzyl;

A is a 5 or 6 membered aromatic carbocyclic or heterocyclic ring;

r is 0, 1 or 2;

s is 0, 1 or 2;

with the exceptions of 4-guanidino-phenylalanine and 4-guanidinomethyl-phenylalanine.

2. A compound according to claim 1 of formula (II)

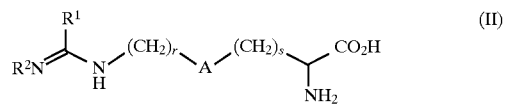

and salts, ester and amides thereof, wherein $R^{1a}$ is a $C_{1-6}$ straight or branched chain alkyl group, a $C_{3-6}$ cycloalkyl group, a $C_{1-6}$ straight or branched chain alkylthio group, or an amino group optionally substituted by one or two alkyl or alkenyl groups;

$R^2$ is H, $C_{1-7}$ straight or branched chain alkyl, $C_{3-6}$ cycloalkyl, $C_{1-7}$ alkenyl, or benzyl;

A is a 5 or 6 membered aromatic carbocyclic or heterocyclic ring;

r is 0, 1 or 2;

s is 0, 1 or 2;

with the exceptions of 4-guanidino-phenylalanine and 4-guanidinomethylphenylalanine.

3. A compound according to claim 1 of formula (IA), (IB) or (IC)

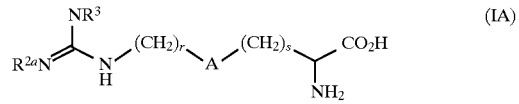

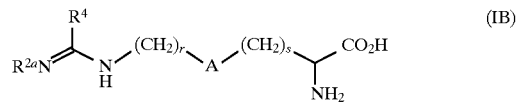

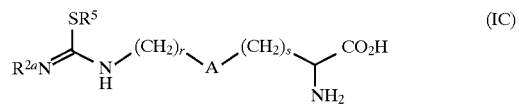

and salts, esters and amides thereof, wherein $R^{2a}$ is H, methyl, ethyl, propyl, isopropyl, $C_{3-6}$ cycloalkyl, allyl or benzyl; $R^3$ is hydrogen, $C_{1-6}$ alkyl, $C_{2-6}$ alkenyl or $C_{3-6}$ cycloalkyl; $R^4$ is a $C_{1-6}$ straight or branched chain alkyl group; $R^5$ is hydrogen or a $C_{1-6}$ straight or branched chain alkyl group; r is 0 or 1; s is 0, 1 or 2; and A is selected from

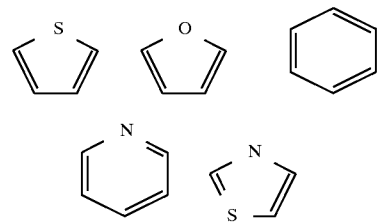

with the exeptions of 4-guanidino-phenylalanine and 4-guanidinomethylphenylalanine.

4. A compound according to claim 1 which is selected from 3-(5-N'-methylguanidino-2-thienyl)-DL-alanine
3-(5-guanidino-2-thienyl)-DL-alanine
2-guanidino-DL-phenylalanine
3-(5-S-ethylisothioureido-2-thienyl)-DL-alanine
3-(5-N'-cyclopropylguanidino-2-thienyl)-DL-alanine
3-(5- N'-allylguanidino-2-thienyl)-DL-alanine
2-thioureido-DL-phenylalanine
2-(S-methylisothioureido)-DL-phenylalanine 2-(S-ethylisothioureido)-DL-phenylalanine
2-(N'-methylguanidino)-DL-phenylalanine
2-(N'-cyclopropylguanidino)-DL-phenylalanine
2-((1-iminoethyl)amino)-DL-phenylalanine
3-guanidino-DL-phenylalanine
3-acetamidino-DL-phenylalanine
4-acetamidino-DL-phenylalanine
3-N-methylguanidino-DL-phenylalanine
4-N-methylguanidino-DL-phenylalanine
3-(5-(1-iminoethyl)amino))-2-thienyl)-DL-alanine
3-(5-N'-methylguanidino)methyl)-2-thienyl)-DL-alanine
3-(5-N'-cyclopropylguanidino)methyl)-2-thienyl)-DL-alanine
3-(5-((S-methylisothioureido)methyl)-2-thienyl)-DL-alanine
3-(5-((S-ethylisothioureido)methyl)-2-thienyl)-DL-alanine
2-(5-S-methylisothioureido-2-thienyl)-DL-glycine
2-(5-S-ethylisothioureido-2-thienyl)-DL-glycine
3-(S-methylisothioureido)-DL-phenylalanine
3-(S-ethylisothioureido)-DL-phenylalanine
4-thioureido-L-phemylalanine
4-(S-methylisothioureido)-L-phenylalanine
4-(S-ethylisothioureido)-L-phenylalanine an salts, esters, and amides thereof.

5. A pharmaceutical formulation for treating a condition requiring inhibition of NO production by the action of NO synthase comprising a compound of formula (I),

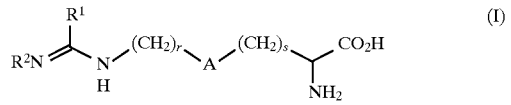

wherein R1 is a $C_{1-6}$ straight or branched chain alkyl group, a $C_{3-6}$ cycloalkyl group, a thiol group optionally substituted by a $C_{1-6}$ alkyl group, or an amino group optionally substituted by one or two alkyl or alkenyl groups;
$R^2$ is H, $C_{1-7}$ straight or branched chain alkyl, $C_{3-6}$ cycloalkyl, $C_{2-7}$ alkenyl, or benzyl;
A is a 5 or 6 membered aromatic carbocyclic or heterocyclic ring;
r is 0, 1 or 2;
s is 0, 1 or 2,
with the exceptions of 4-guanidino-phenylalanine and 4-guanidinomethyl-phenylalanine, and pharmaceutically acceptable salts, esters or amides thereof,
together with one or more pharmaceutically acceptable carriers selected from the group consisting of cocoa butter and polyethylene glycol.

6. A process for the preparation of a compound according to any one of claims 1–4 which comprises:
(a) the deprotection of a compound of formula (III)

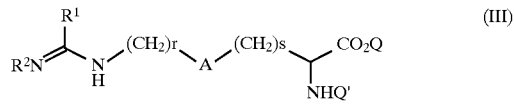

wherein $R^1$, $R^2$, A, r and s are as hereinbefore defined and Q is H or a protecting group and Q' is a protecting group; or (b) the hydrolysis of a compound of formula (VII)

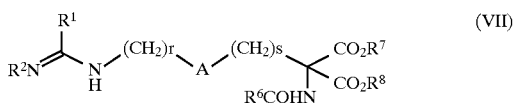

wherein $R^1$, $R^2$, A, r and s are as hereinbefore defined and $R^6$, $R^7$ and $R^8$ are independently selected from $C_{1-4}$ alkyl.

7. A method of treatment of a human or animal body suffering from a condition requiring the inhibition of NO production from L-arginine by the action of NO synthase comprising administering a pharmaceutically effective amount of a compound of formula (I)

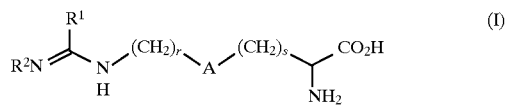

wherein R1 is a $C_{1-6}$ straight or branched chain alkyl group, a $C_{3-6}$ cycloalkyl group, a thiol group optionally substituted by a $C_{1-6}$ alkyl group, or an amino group optionally substituted by one or two alkyl or alkenyl groups;
$R^2$ is H, $C_{1-7}$ straight or branched chain alkyl, $C_{3-6}$ cycloalkyl, $C_{2-7}$ alkenyl, or benzyl;
A is a 5 or 6 membered aromatic carbocyclic or heterocyclic ring;
r is 0, 1 or 2;
s is 0, 1 or 2,
or 4-guanidino-DL-phenylalanine and pharmaceutically acceptable salts, esters and amides thereof to the human or animal body in need of such treatment.

* * * * *

UNITED STATES PATENT AND TRADEMARK OFFICE
CERTIFICATE OF CORRECTION

PATENT NO.   : 5,874,472  
DATED        : February 23, 1999  
INVENTOR(S)  : Shearer et al.

Page 1 of 1

It is certified that error appears in the above-identified patent and that said Letters Patent is hereby corrected as shown below:

Column 26,  
Line 5, in formula (II), please delete the formula

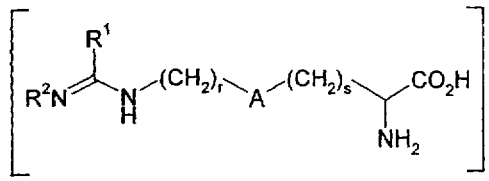

and substitute therefor

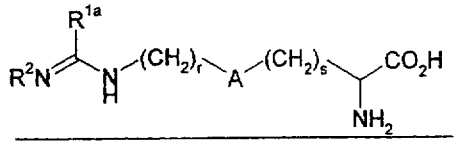

Line 15, delete "$C_{1-7}$" and insert therefor -- $C_{2-7}$ --;

Column 27,  
Line 23, delete "4-thioureido-L-phemylalaline" and insert therefor -- 4-thioureido-L-phenylalanine --;  
Line 36, delete "R1" and insert therefor -- $R^1$ --;

Column 28,  
Line 35, delete "R1" and insert therefor -- $R^1$ --.

Signed and Sealed this

Eighth Day of January, 2002

Attest:

JAMES E. ROGAN  
*Director of the United States Patent and Trademark Office*

*Attesting Officer*